US006143574A

United States Patent [19]
Karlsson et al.

[11] Patent Number: 6,143,574
[45] Date of Patent: Nov. 7, 2000

[54] METHOD OF DETERMINING AFFINITY OR KINETIC PROPERTIES IN SOLUTION

[75] Inventors: Robert Karlsson; Stefan Löfås, both of Uppsala, Sweden; Ralf W. Glaser, Berlin, Germany

[73] Assignee: Biacore AB, Sweden

[21] Appl. No.: 09/068,150

[22] PCT Filed: Nov. 14, 1996

[86] PCT No.: PCT/SE96/01478

§ 371 Date: Oct. 19, 1998

§ 102(e) Date: Oct. 19, 1998

[87] PCT Pub. No.: WO97/18472

PCT Pub. Date: May 22, 1997

[30] Foreign Application Priority Data

Nov. 14, 1995 [SE] Sweden ................................. 9504046

[51] Int. Cl.[7] ...................... G01N 33/557; G01N 33/543; G01N 33/566; G01N 21/00; C12Q 1/00
[52] U.S. Cl. .......................... 436/517; 436/518; 436/512; 436/513; 436/517; 436/169; 436/170; 436/501; 436/527; 436/805; 436/164; 435/4; 435/6; 435/7.1; 435/7.5
[58] Field of Search ...................... 436/518, 517, 436/512, 513, 169, 170, 501, 164, 527, 805; 435/4, 6, 7.1, 7.5

[56] References Cited

U.S. PATENT DOCUMENTS 5,770,462  6/1998  Molloy .................................... 436/527

FOREIGN PATENT DOCUMENTS

WO 90/05305  5/1990  Sweden ................................. 436/517
WO 93/25909  12/1993  United Kingdom .................... 436/517

OTHER PUBLICATIONS

Giesen et al., Monitoring of unbound protein in vesicle suspensions with off–null ellipsometry, Biochimica et Biophysica Acta 1147:125–131 (1993).

Karlsson et al., Kinetic Analysis of monoclonal antigen–antibody interactions with a new biosensor based analytical system, Journal of Immunological Methods, 145:229–240 (1991).

Karlsson et al., Real–Time Compepitive Kinetic Analysis of Interactions between Low–Molecular Weight Ligands in Solution and Surface–Immobilized Receptors, Analytical Biochemistry 221:142–151 (1994).

Paek et al., Modeling of Immunosensors Under Nonequilibrium Conditions, Analytical Biochemistry 196:319–325 (1991).

Azimzadeh et al., "Operational Aspects of Antibody Affinity Constants Measured by Liquid–phase and Solid–phase Assays," *Journal Of Molecular Recognition* 5:9–18, 1992.

National Library of Medicine, file Medline, Medline Accession No. 95397936, Morton et al., "Interpreting complex binding kinetics from optical biosensors: a comparsion of analysis by linearization, the integrated rate equation, and numerical integration," *Anal. Biochem.* 227(1):176–185, 1995. Abstract Only.

National Library of Medicine, file Medline, Medline Accession No. 93289960, Friquet et al., "A radioimmunoassay–based method for measuring the true affinity of a monoclonal antibody with trace amounts of radioactive antigen: illustration with the products of a cell–free protein synthesis system," *Anal. Biochem.* 210(2):344–350, 1993. Abstract Only.

Nelson and Long, "Solution–Phase Equilibrium Binding Interaction of Human Protein S with C4b–Binding Protein," *Biochemistry* 30:2384–2390, 1991.

*Primary Examiner*—James C. Housel
*Assistant Examiner*—Gailene R. Gabel
*Attorney, Agent, or Firm*—Seed Intellectual Property Law Group PLLC

[57] ABSTRACT

A method of determining affinity and kinetic properties for the solution interaction between an analyte and a binding partner therefor, which method comprises: (a) mixing a solution of said analyte with a solution of said binding partner, contacting the resulting reaction solution with (i) immobilised binding partner, or analogue, for said analyte, and/or (ii) immobilised analyte, or analogue, and monitoring the binding of said analyte and/or binding partner in said reaction solution to the respective immobilised species to determine the variation with time of the concentration of free analyte and/or binding partner in said solution; and/or (b) contacting a solution of the reaction complex of said analyte and a binding partner therefor with (i) immobilised binding partner, or analogue, and/or (ii) immobilised analyte, or analogue, and monitoring the binding of said analyte and/or binding partner in said reaction complex solution to the respective immobilised species to determine the variation with time of the concentration of free analyte and/or binding partner resulting from dissociation of said reaction complex in said solution, and from said variation with time of free analyte and/or binding partner determining said affinity and/or kinetic properties.

11 Claims, 1 Drawing Sheet

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 14 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: Modified-site
      (B) LOCATION: 14
      (D) OTHER INFORMATION: /product= "Nle"

(xi) SEQUENCE DESCRIPTION: SEQ ID NO:1:

Gly Pro Gly Gly Gly Ala Thr Pro Gln Asp Leu Asn Thr Xaa
1               5                   10

METHOD OF DETERMINING AFFINITY OR KINETIC PROPERTIES IN SOLUTION

TECHNICAL FIELD

The present invention relates to a method of determining solution affinity and kinetic properties for the formation of a reaction complex between an analyte and a binding partner therefor.

BACKGROUND OF THE INVENTION

Apparatus and methods for investigating the binding of analytes in solution to a receptor are known. Recently, surface sensitive measuring techniques using so-called label-free techniques have been developed for measuring and quantifying biomolecular interactions. In these techniques, a receptor capable of binding to an analyte of interest is immobilised to a sensor surface, and binding of the analyte to the receptor is detected as a resulting change of a property of the sensor surface.

One type of such apparatus (with associated computer control and data-processing means), including the commercial instruments BIAcore and BIAlite (BIAcore and BIAlite are trademarks of Pharmacia Biosensor AB, Uppsala, Sweden; BIA stands for biospecific interaction analysis) has been devised, which uses the phenomenon of surface plasmon resonance (SPR) to study the binding of analytes to receptors immobilized on a sensor chip. The apparatus and theoretical background are fully described in the literature (see e.g. Jönsson, U., et al., BioTechniques 11: 620–627 (1991)). Essentially, the technique involves the immobilisation of a receptor to the special surface of a sensor chip, contacting the sensor chip with a flow of sample containing the analyte of interest, and then measuring the change in the surface optical characteristics of the sensor chip arising form the binding of interest.

With such instrumentation, for example, affinity and kinetic analysis of interactions between soluble analytes and their immobilised binding partners may readily be performed. However, in many cases, it would also be interesting to know the true solution affinity and kinetics of the interaction between two species interacting in solution. So far, such analyses have not been done with the above described type of apparatus.

Friguet, B., et al., Anal. Biochem. 210, 344–350 (1993) discloses the determination of the true affinity constant of a monoclonal antibody for its antigen. Aliquots of radiolabeled antigen at a constant concentration are incubated with the monoclonal antibody at various known concentrations of the antibody in large excess over the antigen. When equilibrium has been reached, the concentration of free antigen is determined by the binding to dextrane beads to which the same monoclonal antibody has been covalently attached. However, this approach only gives information on the equilibrium constant and no kinetic information is provided.

SUMMARY OF THE INVENTION

The object of the present invention is therefore to to provide a method of not only determining true affinity properties but also true kinetic properties for the solution interaction between an analyte and a binding partner therefor to thereby among other things be permitted a wider choice of reaction partners than in solid phase interactions and avoid immobilisation artefacts.

According to the invention, this object is basically achieved by determining the variation of the reaction component concentrations over time in contrast to measuring at equilibrium conditions as in the prior art.

The present invention therefore provides a method of determining affinity and kinetic properites for the solution interaction between an analyte and a binding partner therefor, which method comprises the steps of:

(a) mixing a solution of said analyte with a solution of said binding partner, contacting the resulting reaction solution with (i) immobilized binding partner, or analogue, and/or (ii) immobilised analyte, or analogue, and monitoring the binding of said analyte and/or binding partner in said reaction solution to the respective immobilised species to determine the variation with time of the concentration of free analyte and/or binding partner in said solution; and/or (b) contacting a solution of the reaction complex of said analyte and a binding partner therefor with (i) immobilized binding partner, or analogue, for said analyte, and/or (ii) immobilised analyte, or analogue, and monitoring the binding of said analyte and/or binding partner in said reaction complex solution to the respective immobilised species to determine the variation with time of the concentration of free analyte and/or binding partner resulting from dissociation of said reaction complex in said solution, and from said variations with time of free analyte and/or binding partner determining said affinity and/or kinetic properties.

The term "analogue" with respect to the binding partner means a molecule capable of specifically binding to the analyte in the same way as the binding partner. Similarly, the term "analogue" with respect to the analyte means a molecule capable of specifically binding to the binding partner in the same way as the analyte.

Figure 1:
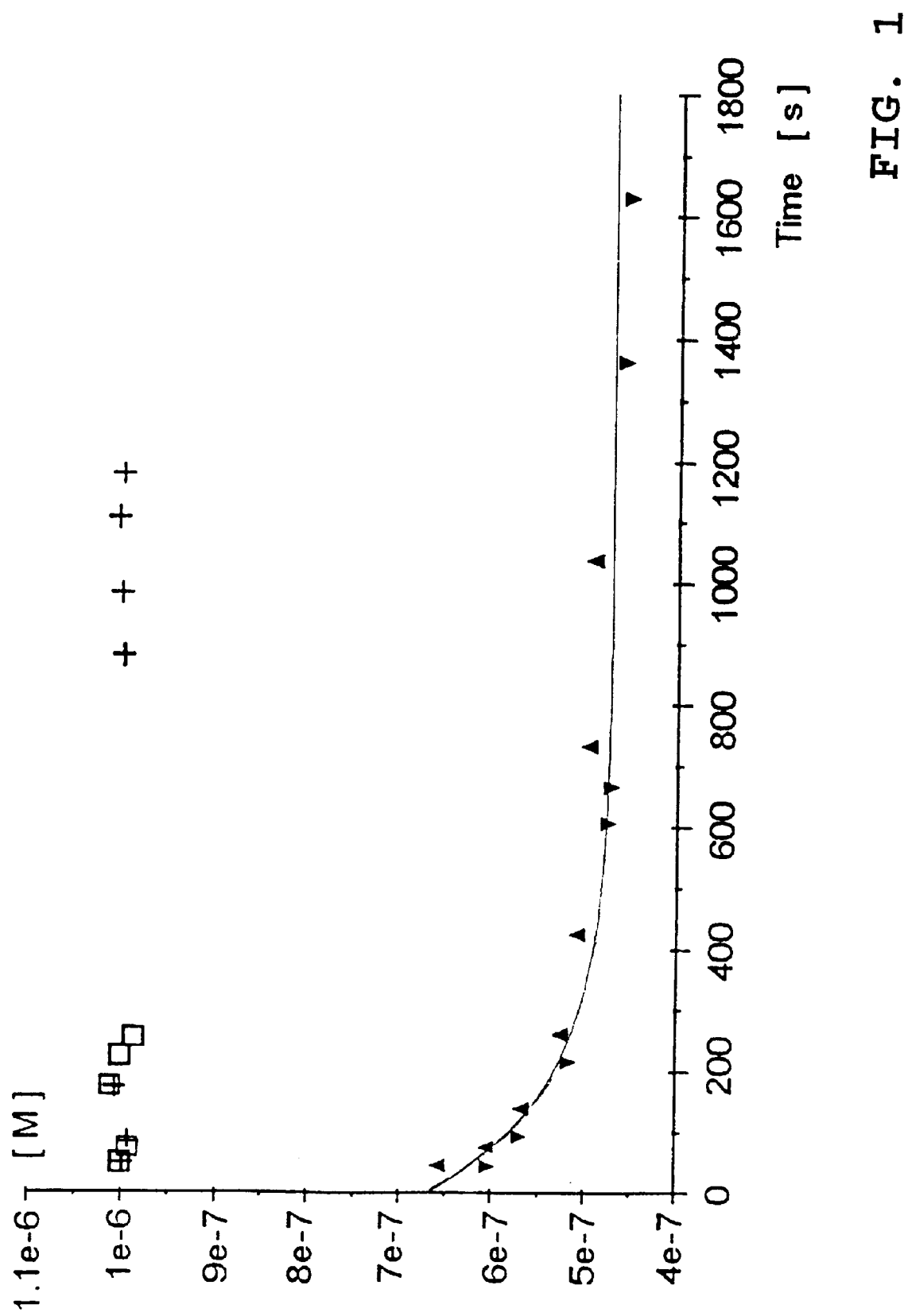
FIG. 1 is a graph showing the concentration of free analyte as a function of time after mixing of an analyte with a binding partner therefor, as determined by binding to a sensor chip coupled with a binding partner for the analyte.

The present invention is based on the concept of determining solution affinity and/or kinetic properties for the interaction between an analyte and its binding partner by using apparatus permitting the analysis of surface interactions. More particularly, the invention is based on measuring the variation of analyte concentrations with time where equilibrium conditions have not been reached.

According to the invention, solution affinity and kinetic properties of the interaction may be determined by mixing the reaction partners with each other and monitoring the free concentration of the analyte by measuring the interaction of the free analyte with a sensor surface supporting a binding partner, or receptor, for the analyte which may be the binding partner or an analogue thereto.

Alternatively, the free concentration of the binding partner may be monitored by measuring the interaction of the free binding partner with a sensor surface supporting the analyte, or an analogue thereto.

In still another alternative, the free concentrations of both the analyte and the binding partner are monitored by measuring their binding to respective sensor surfaces supporting binding partner, or analogue, and immobilized analyte, or analogue, respectively.

In a preferred embodiment, the reaction solution is contacted sequentially with a series of sensor surfaces, so that the reaction solution is first contacted with one sensor surface, and then after some time, for instance 10 seconds to 6 minutes, with another sensor surface, and optionally with one or more additional sensor surfaces after appropriate time delays. The combined measurement results will then give information of analyte and/or binding partner concentration over a wide time range. Preferably, the receptor concentration is the same on the different sensor surfaces. Contacting the sample with several sensor surfaces will also simplify the processing of measurement data as it will only be necessary to measure initial reaction rates.

In one aspect of the invention, association rate characteristics may be analysed by mixing the analyte and the binding partner, and before the reaction mixture has reached equilibrium, contacting the reaction solution with the sensor surface or surfaces.

In another aspect of the invention, dissociation rate characteristics may be analysed by diluting a reacted analyte/binding partner complex at equilibrium and contacting the diluted solution with the sensor surface or surfaces.

The determination of the concentration of free analyte and/or binding partner may be determined by several types of measurements, three of which are mentioned below. In these measurements, the analysis is preferably performed in such a way that only a very small fraction, usually less than 2%, of the free analyte is consumed during analysis.

In a first type of measurement, concentration analysis is performed during mass transfer limiting conditions as is per se known in the art (see e.g. Sjölander, S., and Urbanisczky, C., Anal. Chem. 63: 2938–2345 (1991)). The binding rate is then proportional to the analyte concentration, or expressed in mathematical terms:

$$dR/dt = k*C(t)$$

which may be written as:

$$C(t) = (dR/dt)/k$$

where $\underline{R}$ is the detected response at the sensor surface, $\underline{t}$ is time, $\underline{k}$ is a constant and $\underline{C}$ is concentration of free analyte. dR/dt may be determined from the response curves obtained, and $\underline{k}$ may be determined separately by analysing the binding of known concentrations of analyte to the sensor surface.

In a second type of measurement, the analysis is performed at kinetically controlled conditions. The kinetic parameters of the analyte reacting with immobilised binding partner are determined first in a manner known per se in the art (see e.g. Karlsson, R., et al., J. Immunol. Methods 145: 229–240 (1991)). For instance, for a one to one reaction, the surface reaction is defined by:

$$dR/dt = k_{ass}*C(t)*(R_{max}-R) - k_{diss}*R$$

where $\underline{C}$ is the concentration of free analyte, $\underline{R}$ is the response, $\underline{t}$ is time, $\underline{k}_{ass_1}$ is the association rate constant, $\underline{k}_{diss}$ is the dissociation rate constant, and $\underline{R}_{max}$ is the response corresponding to maximum analyte binding capacity of the sensor surface. Since only C(t) is unknown, it may be calculated by:

$$C(t) = (dR/dt + k_{diss}R)/k_{ass}*(R_{max}-R)$$

In a third type of measurement, an appropriate previously prepared standard curve or curves are used.

It is preferred to perform the measurements in a flow type cell or the like where the reaction solution flows over the sensor surface or surfaces. In such a case, a more accurate or robust analysis may be obtained by carrying out the concentration measurements at varying flow rates (e.g. at 2 and 100 μl/min). This also permits the measurements to be performed at mixed reaction conditions, i.e. where the reaction is neither mass transfer limited nor kinetically controlled.

As mentioned above, when a number of sensor surfaces are used, only the initial reaction rates need be measured whereby the data processing is simplified.

The detection technique used for measuring the interaction of the free analyte with the binding partner immobilised on the sensor surface may be selected from a variety of surface detection methods wherein a resulting change in a property of the sensor surface is measured. Exemplary of such techniques are those based on mass detecting methods, such as piezoelectric, optical, thermo-optical and surface acoustic wave (SAW) methods, and electrochemical methods, such as potentiometric, voltametric, conductometric, amperometric and capacitance methods.

Among optical methods may particularly be mentioned those that detect mass surface concentration or refractive index, such as reflection-optical methods, including both internal and external reflection methods, e.g. ellipsometry and evanescent wave spectroscopy (EWS), the latter including surface plasmon resonance spectroscopy (SPRS), Brewster angle refractometry, critical angle refractometry, frustrated total reflection (FTR), evanescent wave ellipsometry, scattered total internal reflection (STIR), optical wave guide sensors, evanescent wave based imaging, such as critical angle resolved imaging, Brewster angle resolved imaging, SPR angle resolved imaging, etc., as well as methods based on evanescent fluorescence (TIRF) and phosphorescence. Additionally, optical methods based on interference as well as on methods based on surface enhanced Raman spectroscopy and surface enhanced resonance Raman spectroscopy may be mentioned.

In the following, the invention is illustrated by a non-limiting Example which describes analyses of the solution interaction between HIV core protein p24 and antibody CB-4/1.

EXAMPLE

Preparation of Recombinant p24

Recombinant HIV-1 capsid protein p24 was expressed in *E. coli* as described by Hausdorf et al., J. Virol. Methods 50: 1–9 (1994). The N-terminal residues Pro-Ile- of the authentic sequence are replaced in the expression product by Met-Asn-Ser-Ala-Met-, resulting in a protein of 243 amino acid residues, below referred to as rp24.

Preparation of CB-4/1 Fab Fragment

The murine monoclonal IgG 2a/κ antibody CB-4/1/1/F6 (below referred to as CB-4/1) (Grunow et al., Z. Klin. Med. 45, 365–369 (1990)) was produced in a hollow-fiber fermentor as described for the CB-03 antibody by Roggenbuck et al., J. Immunol. Methods 167: 207–218 (1994), and was purified on Protein A. Fab fragments were obtained by papain digestion at 37° C., and Fc fragments and remaining complete antibody were removed on Protein A.

Preparation of Peptide GPGGGATPODLNTX (SEQ ID NO: 1)

The peptide GPGGGATPQDLNTX (X=norleucine SEQ ID NO: 1), a modification of the CB-4/1 epitope on p24, was synthesized on a peptide synthesiser. The peptide obtained was >95% pure as checked by HPLC.

Instrumentation

Measurements were performed with a BIAlite® (Pharmacia Biosensor AB, Uppsala, Sweden). The instrument measures binding between two (or more) molecules in a hydrophilic gel matrix of about 100 nm thickness. One molecule (ligand) is covalently coupled to a carboxymethyldextran-modified gold surface, which allows a restricted diffusion of the ligand. This surface forms one side of a flow chamber, through which a solution of the other molecule (analyte) is flowing. The refractive index change resulting from analyte bound to the ligand in this surface layer is monitored by surface plasmon resonance (Karlsson, R., et al., J. Immunol. Methods 145: 229–240 (1991)). The sensitivity of this method is limited by noise at a resonance signal at about 1 RU (resonance unit) which is equivalent to $10^{-9}$ kg/m$^2$. The time resolution is around 1 second. All measurements were done on a BIAlite® without active temperature control at temperatures between 23° C. and 34° C.

Measurements were performed in 10 mM HEPES buffer, pH 7.4, with 150 mM NaCl, 3.4 mM EDTA and 0.005% v/v surfactant P20 (HBS). Binding curves were analysed with BIAevaluation 2.0 software package (Pharmacia Biosensor AB, Uppsala, Sweden), which allows non-linear fits of the experimental data to standard as well as to user-defined models. Further processing of the obtained parameters was done in EXCEL (Microsoft).

Coupling of GPGGGATPODLNTX (SEQ ID NO: 1) to Sensor Chip

Peptide GPGGGATPQDLNTX (SEQ ID NO: 1) prepared above was coupled to sensor chip CM5 (Pharmacia Biosensor AB, Uppsala, Sweden) at about 180 RU after EDC/NHS chemical modification as described by Johnsson, B., et al., Anal. Bichem. 198: 268–277 (1991). $3.4*10^{-8}$ mol/m$^2$ of the epitope was found to be accessible for CB-4/1 binding. The affinity of the immobilized peptide was $1.4*10^8$ M$^{-1}$.

Study of Binding Kinetics Between CB-4/1 and rp24 in Solution $10^{-6}$ M CB-4/1 Fab was mixed with $1.4*10^{-5}$ M rp24. The mixture was then injected over the above prepared sensor chip coupled with peptide GPGGGATPQDLNTX (X=norleucine), and the concentration of free CB-4/1 Fab was measured at different times after mixing. The flow rate was 20 μl/min, at which rate the binding of CB-4/1 Fab to the chip is mainly limited by mass transport. Under these conditions Fab concentrations between $10^{-7}$ and $2*10^{-6}$ M could be determined with an accuracy better than +/−5%. Measurements were possible under identical conditions every 35 seconds. Two independent experiments and two control experiments without rp24 were performed. The results are presented in FIG. 1 which shows Fab concentration (in M) versus time (s). The two types of filled triangles (▽, Δ) each represent a separate independent experiment, whereas "+" and "□" represent respective control experiments (without rp24). From the binding curve in FIG. 1, the kinetics of the solution interaction could be determined.

What is claimed is:

1. A method for determining affinity and kinetic parameters associated with a first binding interaction between an analyte and a binding partner, wherein the first binding interaction takes place under nonequilibrium conditions in a nonequilibrium solution, comprising the steps of:

forming the nonequilibrium solution in which the first interaction occurs by mixing the analyte and the binding partner to form the nonequilibrium solution, or by causing dissociation of a complex of the analyte and the binding partner to form the nonequilibrium solution;

sequentially contacting the nonequilibrium solution with a plurality of sensor surfaces, each sensor surface having (i) an additional amount of the binding partner or analogue thereof, immobilized thereon, or (ii) an additional amount of the analyte or analogue thereof, immobilized thereon;

monitoring a second binding interaction between (i) the additional amount of the binding partner or analogue thereof immobilized on the plurality of sensor surfaces with the analyte of the nonequilibrium solution, or (ii) the additional amount of the analyte or analogue thereof immobilized on the plurality of sensor surfaces with the binding partner of the nonequilibrium solution, over a period of time;

determining a free analyte or a free binding partner concentration in the nonequilibrium solution at two or more points in time; and therefrom determining the affinity or kinetic parameters associated with the first binding interaction between the analyte and the binding partner.

2. The method according to claim 1, wherein the kinetic parameters are selected from the group consisting of the association rate constant and the dissociation rate constant.

3. The method according to claim 2, wherein the step for determining the dissociation rate constant further comprises diluting the nonequilibrium solution.

4. The method according to claim 1, wherein less than 2% by weight of the analyte binds to the immobilized binding partner over the period of time.

5. The method according to claim 1, wherein the second binding interaction occurs under mass transfer-limited conditions.

6. The method according to claim 1, wherein the second binding interaction occurs under kinetically controlled conditions.

7. The method according claim 1, wherein the step of determining the free analyte or the free binding partner concentration in the nonequilibrium solution comprises the use of one or more standard curves.

8. The method according to claim 1, wherein the plurality of sensor surfaces are optical sensor surfaces.

9. The method according to claim 8, wherein the optical sensor surfaces are part of a detector based upon evanescent wave sensing.

10. The method according to claim 9, wherein the evanescent wave sensing is based on surface plasmon resonance.

11. The method according to claim 1, wherein the step for sequentially contacting the nonequilibrium solution with the plurality of sensor surfaces occurs at at least two different flow rates.

* * * * *